(12) United States Patent
Shan et al.

(10) Patent No.: US 7,091,365 B2
(45) Date of Patent: Aug. 15, 2006

(54) PROCESS FOR OLEFIN EPOXIDATION AND CO-PRODUCTION OF NYLON PRECURSOR

(75) Inventors: Zhiping Shan, Bloomfield, NJ (US); Chuen Y. Yeh, Edison, NJ (US); Philip J. Angevine, Woodbury, NJ (US); Frits M. Dautzenberg, Mahwah, NJ (US); Jacobus Cornelis Jansen, Delft (NL)

(73) Assignee: ABB Lummus Global Inc., Bloomfield, NJ (US)

( * ) Notice: Subject to any disclaimer, the term of this patent is extended or adjusted under 35 U.S.C. 154(b) by 75 days.

(21) Appl. No.: 10/795,726

(22) Filed: Mar. 8, 2004

(65) Prior Publication Data

US 2005/0197499 A1 Sep. 8, 2005

(51) Int. Cl.
*C07D 301/16* (2006.01)
*B01J 21/12* (2006.01)

(52) U.S. Cl. .................................... 549/526; 502/240
(58) Field of Classification Search ................ 549/526; 502/240
See application file for complete search history.

(56) References Cited

U.S. PATENT DOCUMENTS

| | | | |
|---|---|---|---|
| 3,987,100 A | 10/1976 | Barnette et al. | |
| 4,080,387 A | 3/1978 | Jubin et al. | |
| 4,410,501 A | 10/1983 | Taramasso et al. | |
| 4,675,450 A | 6/1987 | Lyon et al. | |
| 5,043,481 A | 8/1991 | Nedwick | |
| 6,358,486 B1 | 3/2002 | Shan et al. | |
| 2002/0074263 A1 | 6/2002 | Shan | |
| 2003/0017943 A1 | 1/2003 | Shan et al. | |

FOREIGN PATENT DOCUMENTS

| | | |
|---|---|---|
| EP | 0 004 105 | 2/1979 |
| EP | 0478331 A | 4/1992 |
| EP | 0 579 323 | 7/1993 |
| EP | 1 209 143 | 5/2002 |
| WO | WO 2004/052537 | 6/2004 |

OTHER PUBLICATIONS

Zhang et al., "Mesoporous Titanosilicate Molecula5r Sieves Prepared at Ambient Temperature by Electrostatic ($S^+I^-$, $S^+X^-I^+$) and Neutral ($S°I°$) Assembly Pathways: A Comparison of Physical Properties and Catalytic Activity for Peroxide Oxidations", *J. Am. Chem. Soc.*, 118, pp. 9164-9171 (1996).

Sheldon et al., "Liquid Phase oxidation at metal ions and complexes in constrained environments", *Catalysis Today*, 41, pp. 387-407 (1998).

*Primary Examiner*—Cecilia J. Tsang
*Assistant Examiner*—Raymond Covington
(74) *Attorney, Agent, or Firm*—Dilworth & Barrese, LLP (57) ABSTRACT

An integrated process combines olefin epoxidation with production of cyclohexanone and cyclohexanol for nylon. Cyclohexanone and cyclohexanol normally produced by the oxidation of cyclohexane, in which cyclohexyl hydroperoxide is generated and is removed or decomposed down stream. However, this invention utilizes the intermediate of cyclohexyl hydroperoxide as an oxidant for the olefin epoxidation and meanwhile generates a valuable product.

20 Claims, 5 Drawing Sheets

PROCESS FOR OLEFIN EPOXIDATION AND CO-PRODUCTION OF NYLON PRECURSOR

BACKGROUND

1. Field of the Invention

The present invention relates to a catalytic conversion process, and particularly to a process for olefin epoxidation with the co-production of a nylon precursor.

2. Background of the Art

Epoxidation of olefin is a well-established reaction, which usually requires heterogeneous catalysts containing transition metals. An early version of commercial catalyst is titanium supported on amorphous silica (cf. R. A. Sheldon, I. WL. C. E. Arends, H. E. B. Lempers, Catal Today 1998, 41, 387–407). If used in an aqueous system the catalytically active component, titanium, leaches out; and the catalyst loses catalytic activity proportionate to the loss of titanium content. Thus, organic oxidants such as tert-butyl hydroperoxide have been used. However, use of tert-butyl hydroperoxide in an organic system leads to the production of alcohol, i.e., tert-butanol, as a reaction byproduct. Reprocessing of this alcohol to its hydroperoxide significantly adds to the production cost of the epoxide.

In 1983 Taramasso et al showed a crystalline microporous titanosilicate (TS-1), isostructural to ZSM-5, exhibited high catalytic activity for olefin epoxidation in either organic or inorganic reaction systems (M. Taramasso, G. Perego, B. Notari, U.S. Pat. No. 4,410,501). While virtually all titanium catalysts leach when exposed to an aqueous environment, the titanium active species in TS-1 is one of the most stable in this regard. TS-1 opened a new area to use hydrogen peroxide as an oxidant, which gives water as a byproduct. Here, this epoxidation process is more environmentally friendly. However, crystalline microporous TS-1 and other transitional metal-containing zeolites have small pores (normally less than 1.2 nm in diameter), which prevent access of some important, bulky reactants to the active sites. For certain large reactants, a catalyst with large pores is required to have good catalytic performance.

Transition metal-containing mesoporous materials (i.e. having pore diameters between 1.5 and 30 nm) have been disclosed, such as Ti-MCM-41 and Ti-MCM-48 (Pinnavaia et al. J. Am. Chem. Soc., 1996, 118, pgs. 9164–1971). These materials have unique pore structures: Ti-MCM-41 possesses one-dimensional pores that are regularly arranged in parallel, whereas Ti-MCM-48 has three-dimensional, ordered pores.

Now, a new mesoporous material (denoted as TUD-1, U.S. Pat. No. 6,358,486 B1) has been disclosed, having a three-dimensionally interconnected pores system. This pore system has advantages over that of MCM-41 because it facilitates mass transfer of reactants and products and reduces the possibility of pore blockage. This mesoporous material can be functionalized by adding transition metals and can then be used as a catalyst for epoxidation.

The TUD-1 mesoporous material mentioned above has an amorphous character. Other, amorphous Ti materials generally have the above-cited leaching problem. Use of an organic medium rather than water can minimize metal leaching, but causes another problem, i.e., formation of undesirable byproduct alcohols. What is needed is a process to effectively utilize the corresponding byproduct alcohol as a valuable product and to permit the use of bulky reactants and organic oxidants for epoxidation without net generation of a co-product alcohol.

SUMMARY

A process for olefin epoxidation is provided herein. The process comprises contacting at least one olefin with an organic hydroperoxide under olefin epoxidation reaction conditions in the presence of a catalyst to provide an epoxidation reaction product containing olefin epoxide(s), wherein the catalyst comprises a transition metal and an amorphous porous inorganic oxide having randomly interconnected mesopores wherein said mesopores comprise at least about 97 volume percent of the pore volume based upon mesopores and micropores, and wherein the porous inorganic oxide is characterized by an X-ray diffraction pattern having a peak between $0.5°$ and $3.0°$ in $2\theta$. Preferably, the organic hydroperoxide is cyclohexyl hydroperoxide, which can be obtained from the oxidation of cyclohexane.

The process utilizes the by-product alcohol to form valuable products such as nylon precursors (e.g., adipic acid and caprolactam).

BRIEF DESCRIPTION OF THE DRAWINGS

Various embodiments are described below with reference to the drawings wherein.

DETAILED DESCRIPTION OF PREFERRED EMBODIMENT(S)

This invention discloses a new integrated process for the epoxidation of olefins and conversion of an organic hydroperoxide to the corresponding alcohol, particularly cyclohexyl hydroperoxide to cyclohexanol. This integrated process can use a transition metal-containing mesoporous material, the transition metals being selected from the group consisting titanium (Ti), chromium (Cr), vanadium (V), iron (Fe), tungsten (W) and molybdenum (Mo) or their combination. It also can use a zeolite-containing mesoporous material, such as that disclosed in U.S. patent application Publication No. 2002/0074263, in which some silicon of the zeolite is isomorphously substituted by Ti, Cr, V, Fe, W, Mo, etc., thereby providing epoxidation activity. This process also can use the combination of two catalytic materials mentioned above, having transition metal(s) in both mesoporous framework and zeolite framework. All three types of catalytic materials have three-dimensionally randomly interconnected mesopores, improving bulky organic accessibility to active sites and reducing mass-transfer limitations.

An advantageous feature of a preferred embodiment of the invention is the production of adipic acid or caprolactam, which are precursors for the subsequent production of nylon. Conventionally, the oxidization of cyclohexane using a gas containing $O_2$ provides a mixture of cyclohexanol, cyclohexanone and cyclohexyl hydroperoxide ("CHHP"). The CHHP then decomposes to cyclohexanol and cyclohexanone. Finally, a mixture of cyclohexanol and cyclohexanone is further oxidized to produce adipic acid. Alternatively, the cyclohexanol can undergo dehydrogenation to form cyclohexanone, the cyclohexanone can react with hydroxylamine to form cyclohexanone oxime, followed by Beckmann rearrangement to obtain caprolactam. The present invention can effectively utilize the intermediate CHHP as an oxidant to oxidize olefin, and meanwhile produce an important, useful alcohol, viz. cyclohexanol. Thus, the CHHP intermediate can be fully used and its decomposition process can be eliminated. Moreover, the epoxidation's alcohol byproduct is a desired chemical precursor for apidic acid or caprolactam production. As such, this invention provides an integrated process, which combines olefin epoxidation and subsequent production of the nylon precursor.

Figure 1:
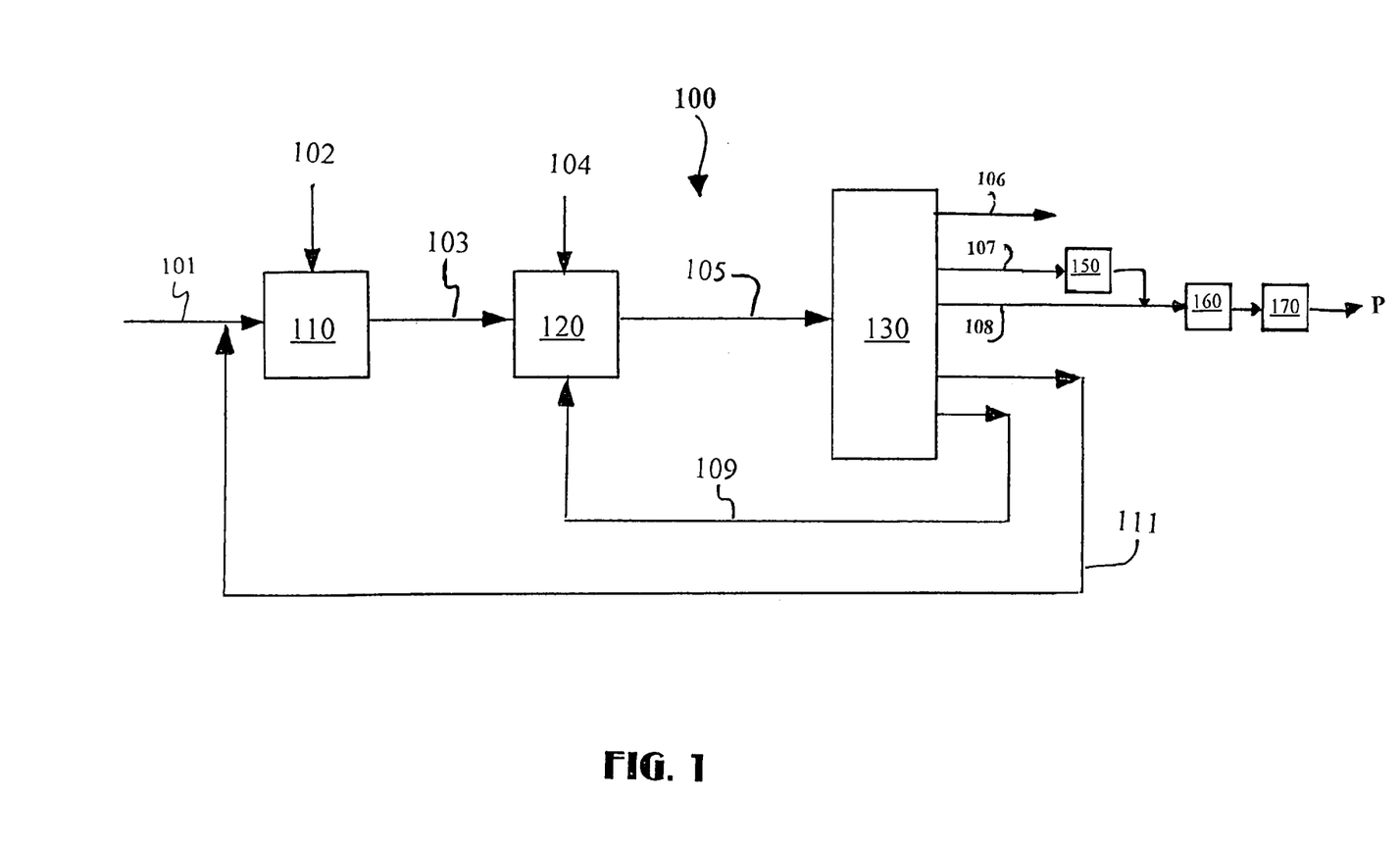
FIG. 1 is a schematic diagram of the process of the present invention.

Referring now to FIG. 1, an integrated system 100 using CHHP for the epoxidation of olefin and co-production of nylon precursor is shown. CHHP can be obtained by cyclohexane oxidation. First, cyclohexane feed 101 is introduced into an oxidation reaction zone 110 where it is oxidized with $O_2$ or $O_2$-containing gas 102 to provide an effluent 103 containing a mixture of CHHP, cyclohexanol, cyclohexanone, and unreacted cyclohexane.

Various methods of cyclohexane oxidation are known in the art. For example, at a temperature between 130° C. and 200° C. and pressure between 4 and 50 bars CHHP can be obtained using an oxygen-containing gas in the absence of a catalyst. U.S. Pat. No. 5,043,481 has similar features of adding oxidation products of cycloalkanes. EP-A-1,209,143 discloses a process using a catalyst comprising a cyclic N-hydroxyimide and a transition metal compound. U.S. Pat. No. 4,675,450 discloses a process using cobalt-containing catalyst in the presence of a phosphate ester. U.S. Pat. No. 3,987,100 discloses a process which uses a cyclohexane-soluble binary catalyst comprising cobalt and chromium salts.

Cyclohexane oxidation normally gives about 2 to 12 wt % CHHP in a mixture of unconverted cyclohexane, cyclohexanol, and cyclohexanone.

Optionally, the CHHP can be first concentrated in the effluent mixture 103 before reacting with olefin by conventional methods. One example of a conventional method includes distillation. For example, U.S. Pat. No. 4,080,387 discloses a method which uses tert-butyl alcohol to form an azeotrope with cyclohexane. Hence, the bottom zone of the distillation column has a concentration of CHHP of about 10 wt. % to 30 wt. %.

The effluent mixture 103 is then introduced into an epoxidation reaction zone 120 where it is contacted with a stream 104 containing the desired olefin(s) in the presence of an epoxidation catalyst. In this step the olefin is partially oxidized to an epoxide, and the CHHP is converted into cyclohexanol.

In principle, an extra solvent for the epoxidation is not necessary because the CHHP-containing effluent 103 has relatively large quantities of cyclohexane and some cyclohexanol and cyclohexanone. Optionally, however, some conventional solvents for epoxidation, such as methanol, can be added to effluent 103 if desired.

Suitable olefins for the integrated process are selected from the group of linear chain, branched chain, or cyclic olefins with carbon number of from 3 to about 25, preferably from 3 to about 16. Suitable olefins include, but are not limited to, propylene, butenes (e.g., 1-butene, 2-butene, isobutene), pentenes, hexenes, heptenes, octenes, nonenes, decenes, cyclohexene, etc. The olefin stream can be a pure olefin, a mixture of two or more olefins, or a mixture of one or more olefins with inert substances.

The preferred epoxidation catalyst is comprises TUD-1, an amorphous mesoporous inorganic oxide having a unique pore structure with three-dimensionally randomly interconnected mesopores. The mesopores comprise at least about 97 volume percent of the pore volume based upon mesopores and micropores. Moreover, its mesopore size can be tuned from 1.5 nm to 30 nm to meet the requirements of various catalytic processes. TUD-1 has been shown to have an unusually high surface area (e.g., 400 to 1100 $m^2/g$) and pore volume (0.4 to 2.0 $cm^3/g$), with the trade-off being pore size. Its X-ray diffraction pattern shows an intensive reflection peak between 0.5 and 3.0 degree in $2\theta$, corresponding to a lattice d-spacing between 25 nm and 350 nm. TUD-1 material has been disclosed in U.S. Pat. No. 6,358,486, which is herein incorporated by reference. The catalyst contains at least one type of transitional metal or could have a combination of several transition metals. Said transition metals include Ti, Cr, V, Fe, Mo, W, Sn, Ga, etc. The amount of the transition metals can be varied from 0.01 wt. % to 90 wt %. The catalyst mainly contains silicon, oxygen and transition metals. However, it might contain some other elements such as aluminum, which can be intentionally added. From a structural point of view, the TUD-1 may further comprise microporous zeolites (e.g., TS-1 and/or TS-2), as disclosed in U.S. patent application Publication No. 2002/0074263, which is herein incorporated by reference. The zeolite may contain transition metals mentioned above in the framework.

Various oxidants can be used for the epoxidation of alkenes, such as molecular oxygen, hydrogen peroxide, organic hydroperoxide (e.g. tert-butyl hydroperoxide) and organic peracids (e.g. peroxyformic acid). While many different alkyl hydroperoxides can be employed in this general reaction system, cyclohexyl hydroperoxide (CHHP) is preferable according to this specific invention. It is preferably used in organic reaction systems, with minimal water in the reaction system.

In the epoxidation reaction zone 120 the olefin stream is contacted with a CHHP-containing stream in the presence of an epoxidation catalyst at a temperature of from about 0° C. to about 200° C. and a pressure up to about 100 bars, preferably a temperature of from about 20° C. to about 80° C. and a pressure of from about atmospheric to about 30 bars. The epoxidation effluent 105 contains epoxide, cyclohexanol, cyclohexanone, unreacted olefin, and unreacted cycloalkane. Separation can then be carried out by, for example, distillation, at separation stage 130 to obtain the desired products of epoxide 106, cyclohexanol 107 and cyclohexanone 108, or a mixture of cyclohexanol and cyclohexanone (also known as "KA oil"). The unconverted olefin is returned to the epoxidation reaction zone 120 via olefin recycle stream 109, and unreacted cyclohexane is returned to the oxidation reaction zone 110 via cyclohexane recycle stream 111.

The cyclohexanol 107 is preferably sent to a dehydrogenation reaction zone 150 where it undergoes dehydrogenation under conventional reaction conditions to produce cyclohexanone, which is then added to cyclohexanone stream 108. The cyclohexanone 108 is then sent to an ammoxidation reaction zone 160 where it is reacted with hydroxylamine and converted into cyclohexanone oxime. The cyclohexanone oxime is then sent to reaction zone 170 where it is converted by Beckmann rearrangement to caprolactam, a nylon precursor, which is drawn off as a valuable product P. Dehydrogenation, ammoxidation and Beckmann rearrangement are conventional processes known in the art.

In an alternative embodiment, the KA oil mixture of cyclohexanol and cyclohexanone can be oxidized to provide adipic acid, $HOOC(CH_2)_4COOH$, another nylon precursor. Processes for the oxidation of KA oil with, for example, nitric acid are known in the art.

The following Examples are provided to illustrate the invention. X-ray power diffraction (XRD) patterns of the resulting materials were recorded using on a Philips PW 1840 diffractometer (with $CuK_\alpha$ radiation) equipped with a graphite monochromator. The samples were scanned in the range of 0.5–40° 2θ with steps of 0.02°. Transmission electron microscope (TEM) measurements were performed using a Philips CM30T electron microscope with a LaB6 filament as the electron source operated at 300 kV. Nitrogen sorption isotherms were measured at 77° K on a Quantachrome Autosorb-6B. Mesoporosity was calculated using the BJH (Barrett-Joyner-Halenda) model. Gas Chromatography (GC) analysis was conducted using WAX 52 CB.

EXAMPLE 1

First, 1.1 parts by weight of titanium (IV) n-butoxide (purity 99%, ACROS) was mixed with 35.0 parts by weight of tetra ethyl orthosilicate ("TEOS") (98+%, ACROS). Then, 25.3 parts of triethanolamine ("TEA") (97%, ACROS) was added drop-wise into the above mixture while stirring. After 1 hr of stirring, 17.3 parts of tetraethylammonium hydroxide ("TEAOH") (25%, Aldrich) was added drop-wise into the above mixture. The final homogenous mixture was aged at room temperature for 24 hr, dried at 100° for 24 hr and then calcined at 700° C. for 10 hr with a heating ramp rate of 1° C. $min^{-1}$ in air.

Figure 2:
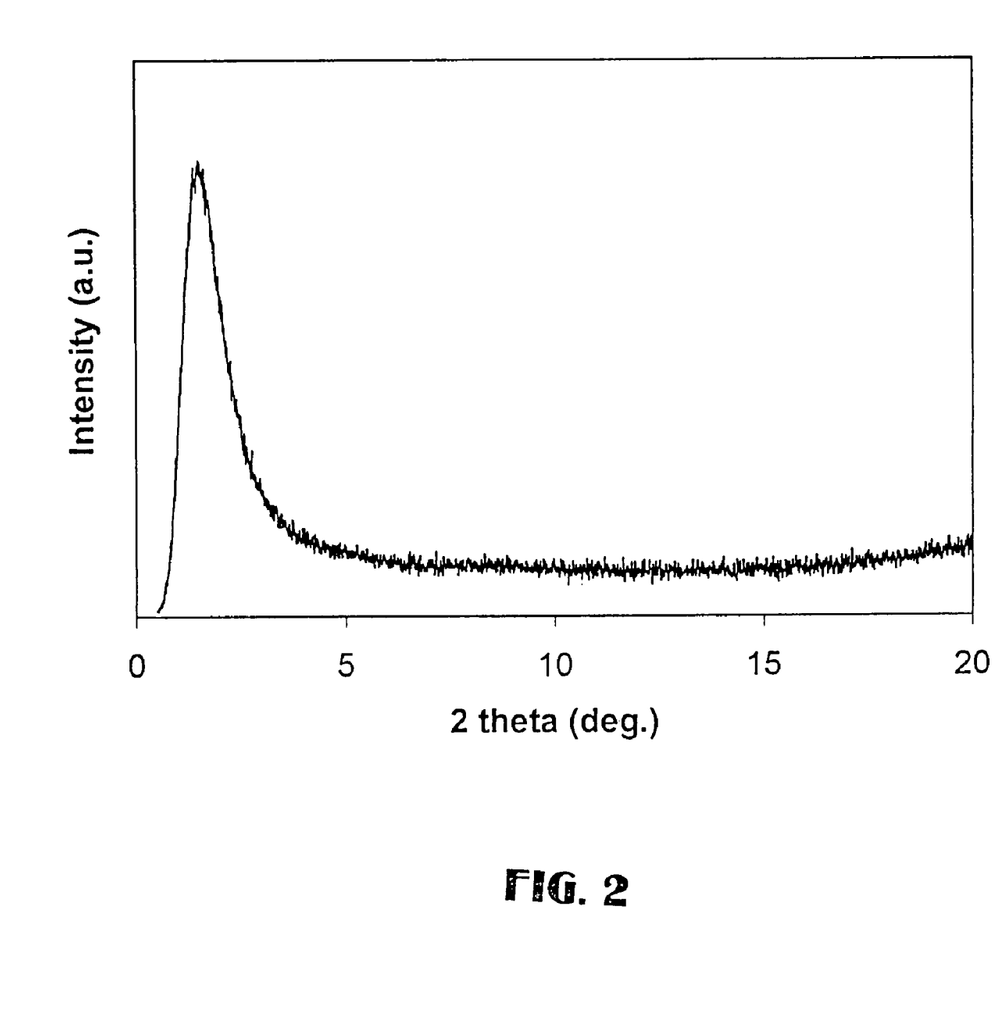
FIG. 2 is an X-ray diffraction pattern of the material obtained in Example 1.
Figure 3:
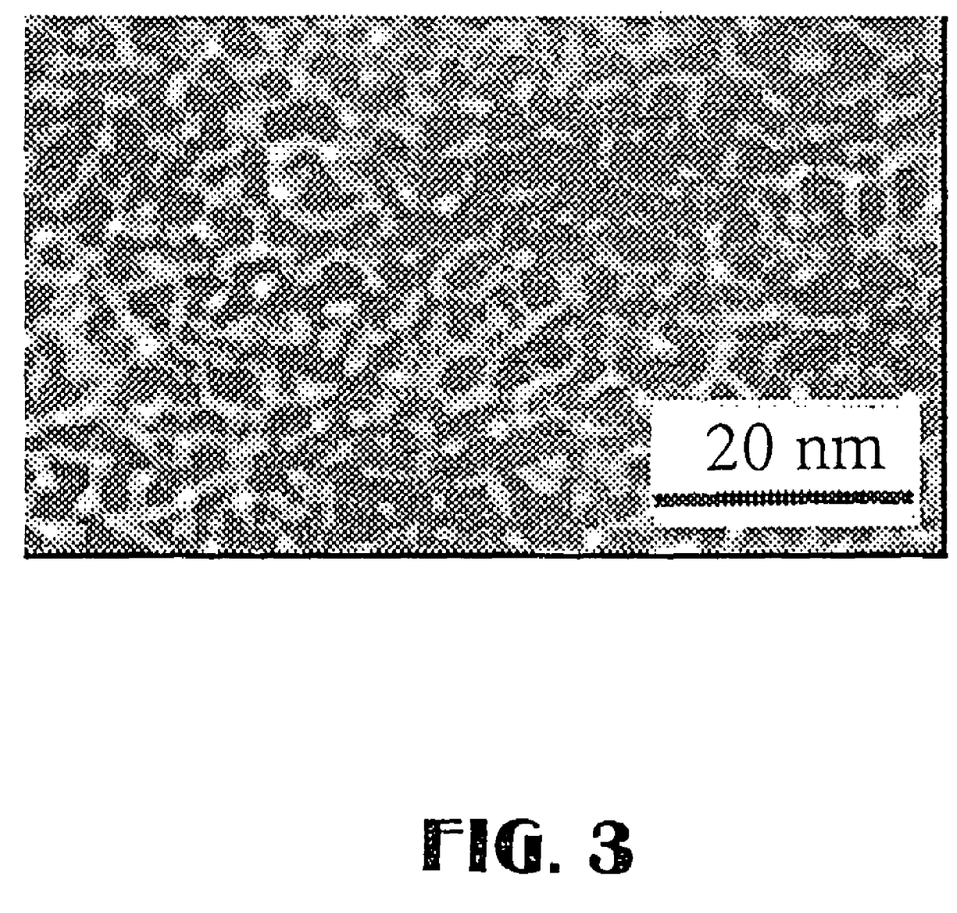
FIG. 3 is a TEM image of the material obtained in Example 1.
Figure 4:
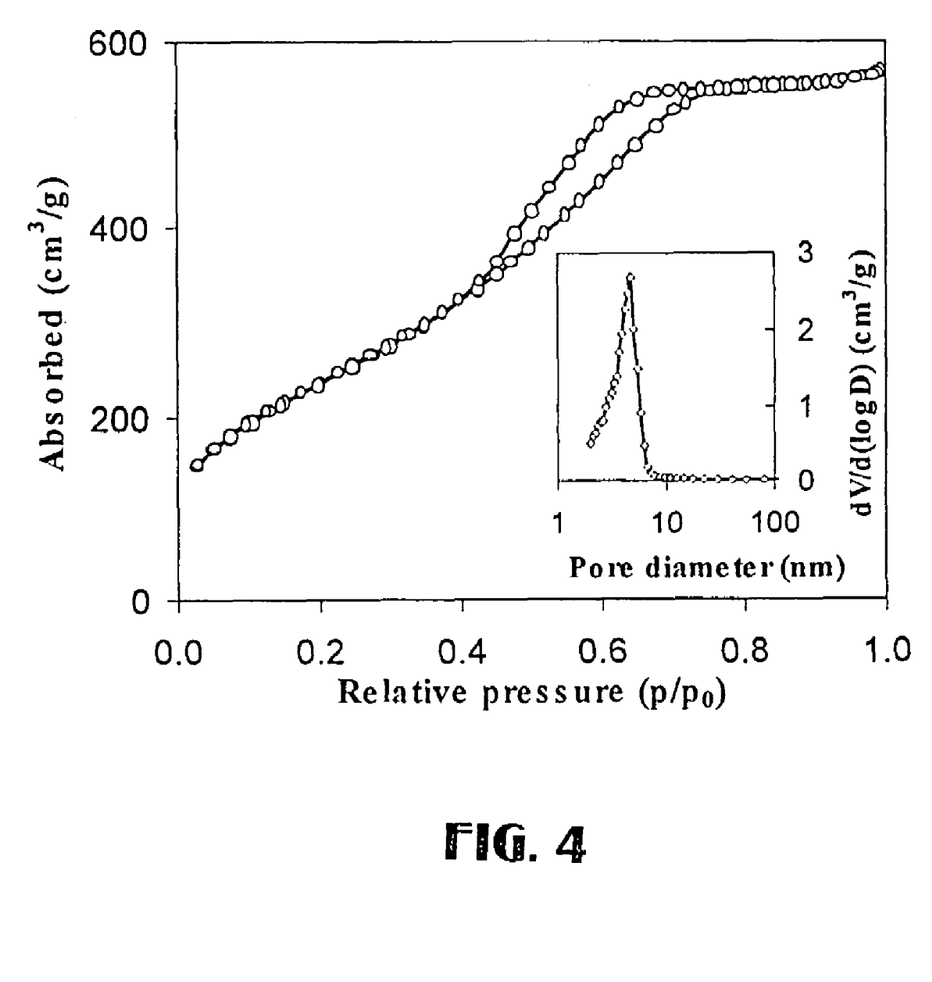
FIG. 4 depicts the nitrogen adsorption isotherms and pore size distribution for the material obtained in Example 1.

The XRD pattern of the resulting material, depicted in FIG. 2, shows only one intensive peak at about 1.0° in 2θ, indicating it is a meso-structured material. The TEM image in FIG. 3 show that curved and tortuous pores are randomly connected to form a three-dimensional pore network. Nitrogen adsorption revealed its BET surface area of 917 $m^2/g$, an average mesopore diameter 4.5 nm and total pore volume of 0.89 $cm^3/g$, as shown in FIG. 4.

EXAMPLE 2

Figure 5:
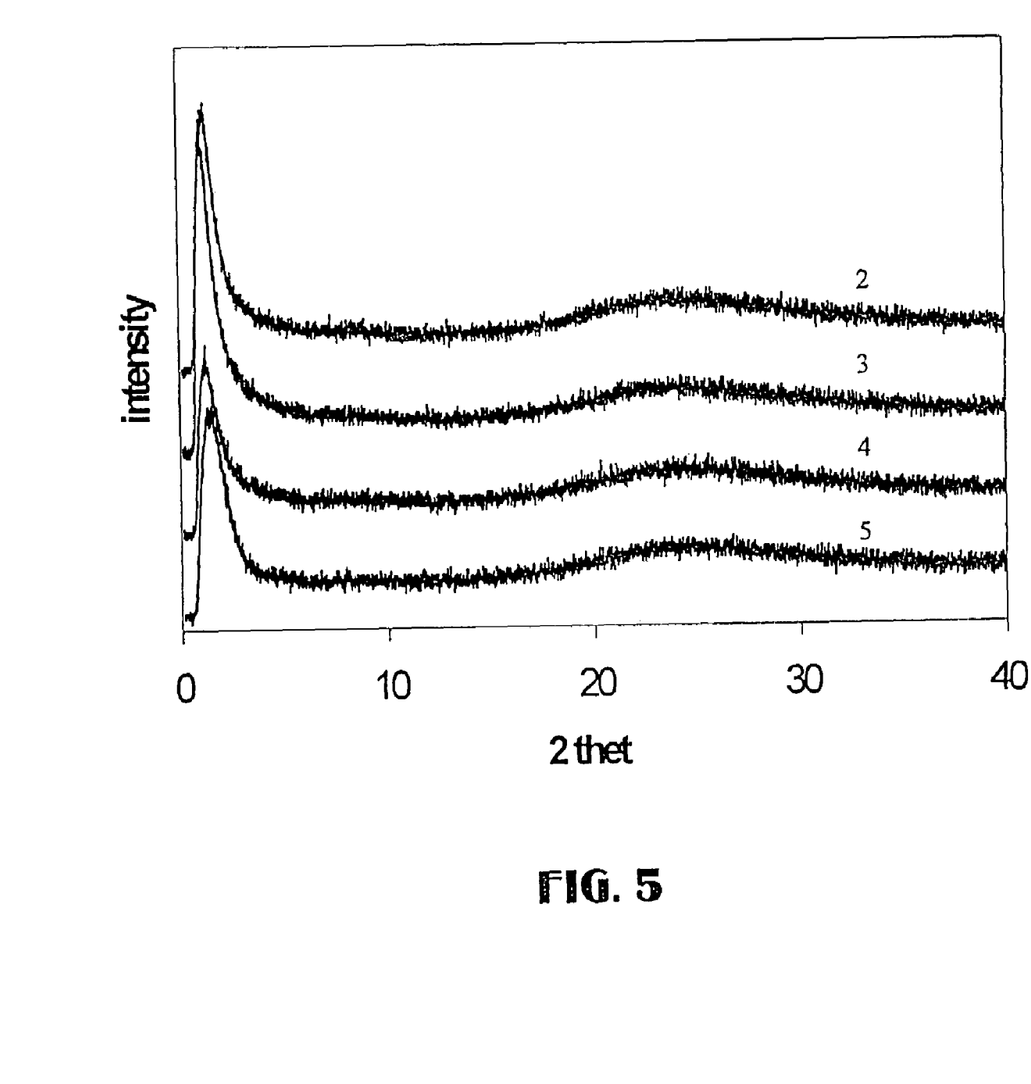
FIG. 5 shows the X-ray diffraction patterns of the materials obtained in Examples 2, 3, 4 and 5.

1.7 Parts of titanium (IV) n-butoxide (99%) were mixed with 106 parts of TEOS (98%). Then a mixture of 77 parts TEA (97%) and 58 parts of deionized water was added drop-wise into the above mixture while stirring. After about 1 hr stirring, 63 parts of TEAOH (25%) were added drop-wise to the mixture. The synthesis mixture's Si/Ti molar ratio was 100. The final, homogeneous mixture was aged at room temperature for 24 hours, dried at 98° C. for 24 hours and then calcined at 650° C. for 10 hours at a heating ramp rate of 1° C./min in air. The XRD pattern of the material is shown in FIG. 5.

EXAMPLE 3

The same procedure as in Example 2 was followed except that 3.4 parts by weight of titanium (IV) n-butoxide were used, and the mixture's Si/Ti ratio was 50. The XRD pattern of the resulting material is shown in FIG. 5.

EXAMPLE 4

The same procedure as in Example 2 was followed except that 8.6 parts of titanium (IV) n-butoxide were used, and the reactant mixture Si/Ti ratio was 20. The XRD pattern of the resulting material is shown in FIG. 5.

EXAMPLE 5

The same procedure as in Example 2 was followed; however, 17.2 parts of titanium (IV) n-butoxide were used, and the reactant mixture Si/Ti ratio was 10. The XRD pattern of the resulting material is shown in FIG. 5.

As can be seen, adding the appropriate amounts of titanium compound in the initial synthesis mixture can easily control the titanium loading of the catalyst material of the present invention (Examples 2–5). The XRD patterns of the resulting materials of Examples 2–5 indicate that these materials are mesoporous.

EXAMPLE 6

This example demonstrates the auto-oxidation of cyclohexane to cyclohexyl hydroperoxide. In a Teflon® lined autoclave, 15 parts of cyclohexane by weight, 1 part of chlorobenzene as internal standard and 0.01 parts of dicumyl peroxide as initiator were charged. Into the mixture in the autoclave, a gas mixture of oxygen and nitrogen having an oxygen concentration of 8% by volume was fed for one hour at a rate of 50 ml/min, and then pressurized to about 10 bars. The mixture was heated up to 120° C., and the pressure was adjusted to 15 bars using the above-mentioned oxygen-containing nitrogen gas.

In the course of the reaction, oxygen was gradually consumed, and the pressure dropped. After every hour, the pressure was adjusted to 15 bars by refilling oxygen-containing nitrogen. After 22 hours, the reaction was stopped by cooling and depressurizing. Upon cooling to room temperature, the reaction mixture was recovered for analysis and subsequent epoxidation.

GC analysis was used to measure cyclohexanone, cyclohexanol, and CHHP content. The CHHP content was also confirmed via titration with $Na_2S_2O_3$ solution. The final reaction mixture had cyclohexanone (0.50 wt %), cyclohexanol (0.76 wt %) and cyclohexyl hydroperoxide (6.3 wt %). The conversion of cyclohexane was 6.2 wt %, and a selectivity to cyclohexyl hydroperoxide was 76.4 wt %. The final reaction mixture was dried using anhydrous $MgSO_4$ before the epoxidation reaction.

EXAMPLE 7

The procedure is the same as Example 6, but the reaction was held at 150° C., and the reaction time was shortened to 4.5 hr. Finally the reaction mixture contained cyclohexanone (0.47 wt. %), cyclohexanol (0.74 wt. %) and cyclohexyl hydroperoxide (6.8 wt. %). The conversion of cyclohexane was 7.6 wt. %, and the selectivity to cyclohexyl hydroperoxide was 84.9 wt. %.

EXAMPLE 8

The procedure was the same as in Example 6, but the reaction temperature was held at 160° C., and the reaction time was shortened to 0.5 hr. The reaction mixture contained cyclohexanone (0.12 wt. %), cyclohexanol (0.34 wt. %) and cyclohexyl hydroperoxide (4.8 wt. %). The conversion of cyclohexane was 4.4 wt. %, and the selectivity to cyclohexyl hydroperoxide was 85.3 wt. %.

EXAMPLE 9

This example demonstrates epoxidation of 1-octene. The catalyst prepared in Example 1 was dried in an oven at 180° C. overnight in air. 1 part (by weight) of dried catalyst was transferred into a flask in an oil bath with a temperature controller. The flask, connected to a vacuum system, was heated up to 140° C. under vacuum for 2 hr to remove any moisture. The catalyst was then cooled to 80° C. under flowing nitrogen. After the temperature was stable, 4 parts of 1-octene and 28 parts of the reaction product from Example 6 were injected into the flask under a nitrogen blanket.

After a reaction for 20 hr, the reaction mixture was analyzed by GC. Almost all of the CHHP was converted (1-octene conversion was about 42 wt. %) with a 1-octene oxide selectivity of about 90% based on CHHP conversion. Finally, the reaction mixture contained about 6.4 wt. % cyclohexanone and cyclohexanol, 4.6 wt. % 1-octene oxide, 81 wt. % of cyclohexane and 7.0 wt. % of 1-octene.

EXAMPLE 10

Epoxidation of 1-octene was conducted in the same procedures as Example 9. However, here the reaction mixture containing cyclohexyl hydroperoxide was from Example 8.

After the reaction for 48 hr, the reaction mixture was analyzed by GC. Almost all of the CHHP was converted with selectivity to 1-octene oxide of 89%. The conversion of 1-octene reached about 32 wt. % with a selectivity to 1-octene oxide of about 98.5 wt. %.

EXAMPLE 11

Propylene is used as a reactant to demonstrate the production of propylene oxide using CHHP. A reaction mixture of concentrated CHHP is used as an oxidant and solvent, which has 20 wt. % cyclohexyl hydroperoxide, 2 wt. % cyclohexanone, 2 wt. % cyclohexanol and 76 wt. % cyclohexane. The catalyst prepared in Example 3 is dried at 180° C. overnight. Five (5) parts of the catalyst are transferred into a Teflon-lined batch reactor under flowing nitrogen. The batch reactor is heated up to 180° C. under nitrogen flow for 0.5 hr and subsequently cooled at 80° C. One hundred (100) parts of the reaction mixture containing 20 wt. % of CHHP is charged into the reactor under stirring. Then the reactor is pressurized using dried propylene to 20 bars. As the gaseous reactant become a liquid, the pressure dropped due to propylene consumption. After every hour of reaction propylene is refilled to resume the total pressure of 20 bars.

After 12 hr the reaction mixture is analyzed by GC. The reaction mixture contains 7.6 wt. % propylene oxide, 19.9 wt. % cyclohexanone and cyclohexanol, and about 0.9 wt. % CHHP. The conversion of CHHP is about 95%, and the selectivity to propylene oxide is about 85%.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A process for olefin epoxidation comprising:
   contacting at least one olefin with cyclohexyl hydroperoxide under olefin epoxidation reaction conditions in the presence of a catalyst to provide an epoxidation reaction effluent containing olefin epoxide, wherein said catalyst comprises a transition metal and an amorphous porous inorganic oxide having randomly interconnected mesopores, wherein said mesopores range in diameter from about 1.5 to about 30 nm and comprise at least about 97 volume percent of the pore volume based upon mesopores and micropores, and wherein said porous inorganic oxide is characterized by an X-ray diffraction pattern having a peak between 0.50 and 3.00 in $2\theta$, and wherein said porous inorganic oxide has a surface area of from about 400 to 1,100 $m^2/g$.

2. The process of claim 1 wherein said olefin has a carbon number of from 3 to 25.

3. The process of claim 1 wherein said olefin has a carbon number of from 3 to 16.

4. The process of claim 1 wherein said olefin is selected form the group consisting of propylene, 1-butene, 2-butene, isobutene, pentenes, hexenes, heptenes, octenes, nonenes, decenes, cyclohexene and combinations thereof.

5. The process of claim 1 wherein the olefin epoxidation reaction conditions include a temperature of from about 0° C. to about 200° C. and a pressure up to about 100 bars.

6. The process of claim 1 wherein the transition metal is selected from the group consisting of Ti, Cr, V, Fe, Mo, W, Sn and Ga.

7. The process of claim 5 wherein the transition metal is Ti.

8. The process of claim 1 wherein the catalyst further comprises a microporous crystalline zeolite.

9. The process of claim 8 wherein the zeolite is selected from the group consisting of TS-1 and TS-2.

10. The process of claim 1 wherein the cyclohexyl hydroperoxide is provided by the oxidation of cyclohexane.

11. The process of claim 10 wherein the cyclohexyl hydroperoxide is provided in a stream further containing cyclohexanol and cyclohexanone.

12. The process of claim 1 wherein the epoxidation reaction effluent further contains cyclohexanol and cyclohexanone.

13. The process of claim 12 wherein the cyclohexanol and cyclohexanone in the effluent are oxidized to provide adipic acid.

14. The process of claim 12 wherein the cyclohexanone in the effluent is converted by ammoxidation to cyclohexanone oxime, which is then converted to caprolactam by Beckmann rearrangement.

15. The process of claim 14 wherein the cyclohexanol in the effluent is dehydrogenated to form additional cyclohexanone, which is then combined with the cyclohexanone in the effluent prior to ammoxidation.

16. An integrated process for the production of nylon precursor comprising the steps of:
   a) oxidation of cyclohexane in a first oxidation reaction zone with an oxygen-containing gas to provide a first intermediate stream containing cyclohexyl hydroperoxide, cyclohexanol and cyclohexanone;
   b) contacting at least one olefin with the cyclohexyl hydroperoxide under olefin epoxidation reaction conditions in the presence of a catalyst wherein said catalyst comprises a transition metal and an amorphous porous inorganic oxide having randomly interconnected mesopores, wherein said mesopores range in diameter from about 1.5 to about 30 nm and comprise at least about 97 volume percent of the pore volume based upon mesopores and micropores, and wherein said porous inorganic oxide is characterized by an X-ray diffraction pattern having a peak between 0.50 and 3.00 in 2θ, and wherein said porous inorganic oxide has a surface area of from about 400 to 1,100 m²/g, to provide an epoxidation reaction effluent containing olefin epoxide, cyclohexanol and cyclohexanone, c) separating the olefin epoxide from the epoxidation reaction effluent; and, d) converting the cyclohexanol and/or cyclohexanone in the epoxidation reaction effluent to a nylon precursor.

17. The process of claim 16 wherein the cyclohexanol and cyclohexanone in the epoxidation reaction effluent are oxidized and the nylon precursor is adipic acid.

18. The process of claim 16 wherein the nylon precursor is caprolactam, which is provided by the ammoxidation of epoxidation reaction effluent cyclohexanone to produce cyclohexanone oxime, and the Beckmann rearrangement of the cyclohexanone oxime to produce the caprolactam nylon precursor.

19. The process of claim 16 wherein the transition metal is titanium.

20. The process of claim 16 wherein the said catalyst further comprises at least one zeolite with amorphous substituted titanium.

* * * * *